(12) United States Patent
Crea

(10) Patent No.: US 10,178,869 B2
(45) Date of Patent: Jan. 15, 2019

(54) **TREATMENT OF *ELAEIS* FRUIT PRODUCTS WITH ANTIOXIDANTS**

(76) Inventor: Roberto Crea, Hayward, CA (US)

( * ) Notice: Subject to any disclaimer, the term of this patent is extended or adjusted under 35 U.S.C. 154(b) by 657 days.

(21) Appl. No.: 13/984,995

(22) PCT Filed: Feb. 13, 2012

(86) PCT No.: PCT/US2012/024890
§ 371 (c)(1),
(2), (4) Date: Jul. 24, 2014

(87) PCT Pub. No.: WO2012/109662
PCT Pub. Date: Aug. 16, 2012

(65) Prior Publication Data
US 2015/0050365 A1    Feb. 19, 2015

Related U.S. Application Data

(60) Provisional application No. 61/441,979, filed on Feb. 11, 2011.

(51) Int. Cl.
| A61K 36/63 | (2006.01) |
| A23D 7/06 | (2006.01) |
| A61K 31/05 | (2006.01) |
| A61K 36/889 | (2006.01) |
| A01N 65/40 | (2009.01) |
| A61K 8/34 | (2006.01) |
| A61K 8/97 | (2017.01) |
| C11D 3/382 | (2006.01) |
| A23L 33/105 | (2016.01) |
| A61Q 19/00 | (2006.01) |

(52) U.S. Cl.
CPC .............. *A23D 7/06* (2013.01); *A01N 65/40* (2013.01); *A23L 33/105* (2016.08); *A61K 8/345* (2013.01); *A61K 8/97* (2013.01); *A61K 31/05* (2013.01); *A61K 36/889* (2013.01); *A61Q 19/00* (2013.01); *C11D 3/382* (2013.01); *A23V 2002/00* (2013.01); *A61K 2236/31* (2013.01); *A61K 2800/10* (2013.01)

(58) Field of Classification Search
None
See application file for complete search history.

(56) References Cited

U.S. PATENT DOCUMENTS

| 5,714,150 A | 2/1998 | Nachman |
| 6,165,475 A | 12/2000 | Crea et al. |
| 6,197,308 B1 | 3/2001 | Crea et al. |
| 6,416,808 B1 * | 7/2002 | Crea ...................... A01N 31/08 426/601 |
| 7,261,909 B2 | 8/2007 | Crea |
| 7,713,569 B2 * | 5/2010 | Crea ...................... A01N 31/16 424/769 |
| 2003/0108651 A1 | 6/2003 | Crea |
| 2007/0269400 A1 * | 11/2007 | Golz-Berner ............ A61K 8/97 424/74 |
| 2008/0188551 A1 | 8/2008 | Roesler et al. |
| 2009/0252817 A1 | 10/2009 | Hayes et al. |
| 2012/0121732 A1 * | 5/2012 | Hj. Che Idris ....... A61K 31/355 424/727 |

FOREIGN PATENT DOCUMENTS

WO    WO-2010134799 A1 *    11/2010    ........... A61K 31/355

OTHER PUBLICATIONS

Visioli et al. (2000) Circulation, 102:2169-2171.*
Yin et al. (2013) Inter. J. Pharmacy and Pharma. Sci. vol. 5, Suppl. 4, 137-140.*
Bakar (Nov. 2006) "Study on Mechanical Pretreatment Process of Palm Oil Mill Effluent (POME)," University of College of Engineering & Technology Malaysia. pp. 1-27.
Sies et al. (1997) "Oxidative stress: Oxidants and antioxidants," Exp. Physiol. 82(2):291-295.
International Search Report with Written Opinion corresponding to International Patent Application No. PCT/US2012/024890, dated Oct. 24, 2012.

* cited by examiner

*Primary Examiner* — Christopher R Tate
*Assistant Examiner* — Russell G Fiebig
(74) *Attorney, Agent, or Firm* — Lathrop Gage LLP

(57) ABSTRACT

Methods are disclosed to create healthier palm oil and new food additives derived from products of the processing of *Elaeis* fruit that were hitherto fore discarded as waste. The pressing product of *Elaeis* fruit and the effluent created is treated with acidified antioxidants from olive vegetation containing hydroxytyrosol and a mixture of other polyphenols. The treated POME, palm oil and palm juice are stabilized against oxidation and their inherently nutritive components may now be harvested instead of being thrown away.

10 Claims, 1 Drawing Sheet

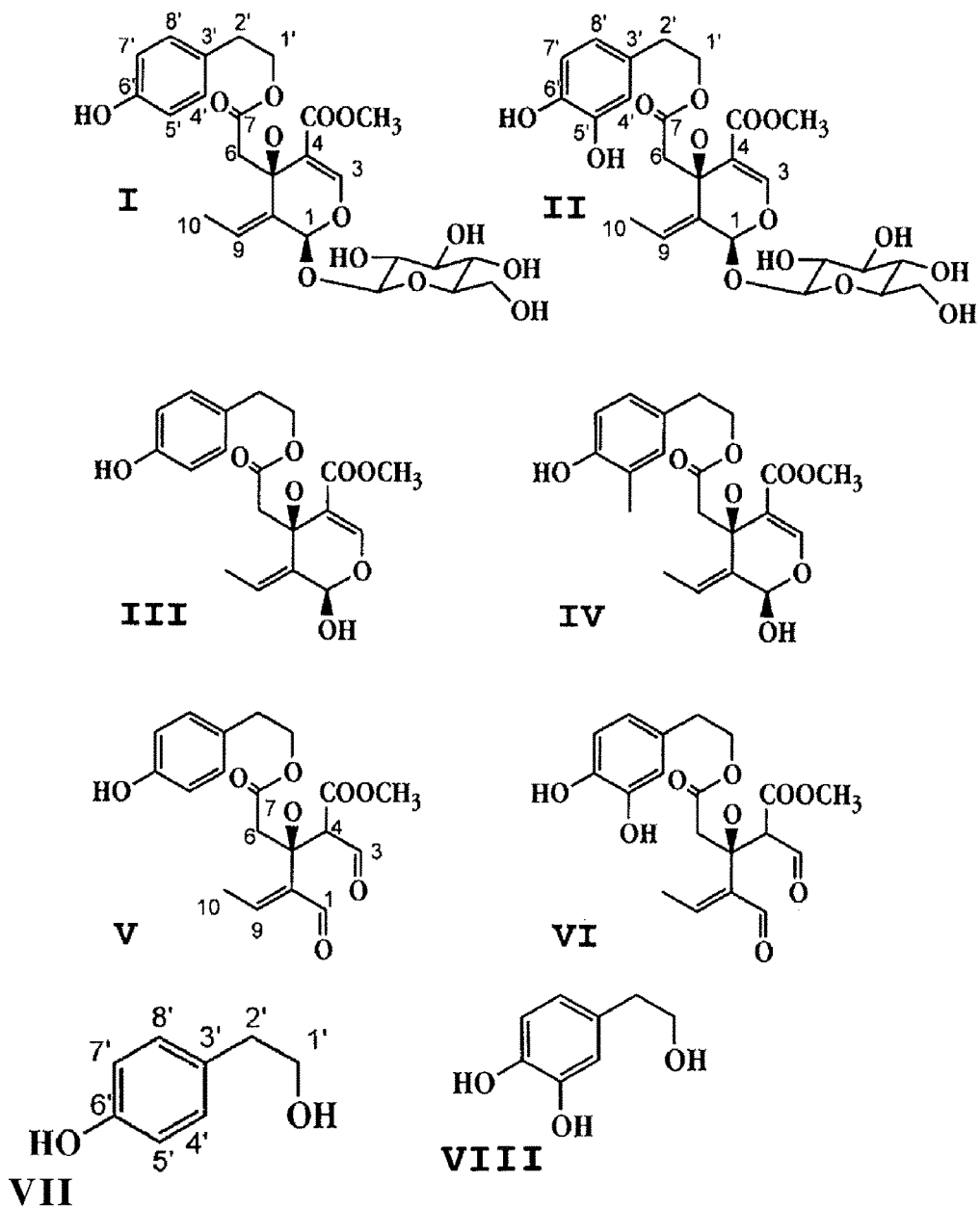
Antioxidant structures of phenolic compounds found in olive oil: ligstroside (I); oleuropein glucoside (II); aglycone of ligstroside (III); aglycone of oleuropein glucoside (IV); dialdehydic form of ligstroside aglycone lacking a carboxymethyl group (V); dialdehydic form of oleuropein glucoside aglycone (VI); tyrosol (VII); hydroxytyrosol (VIII)

TREATMENT OF *ELAEIS* FRUIT PRODUCTS WITH ANTIOXIDANTS

RELATED APPLICATIONS

This application is a 35 U.S.C. § 371 filing of International Application No. PCT/US2012/024890 filed Feb. 13, 2012, which claims priority from U.S. Provisional Patent Application No. 61/441,979, filed on Feb. 11, 2011. The entire contents of each of the above documents are incorporated herein by reference.

BACKGROUND

Palm oil is an important global commodity. Palm oil is derived from oil palms, *Elaeis*. *Elaeis* are two species of the Arecacae, or palm family. The African oil palm *Elaeis guineensis* is native to West Africa, occurring between Angola and Gambia, while the American oil palm *Elaeis oleifera* is native to tropical Central America and South America. *Elaeis*, herein, is used to refer to any oil palm and *Elaeis* and palm are used interchangeably.

Three edible oils are derived from *Elaeis*. The three oils come from different parts of the plant. Coconut oil is extracted from the kernel of the coconut, palm oil is extracted from the pulp of *Elaeis* fruit and palm kernel oil is extracted from the kernel of *Elaeis* fruit. Palm oil as used herein will generally refer to the oil extracted from the pulp of *Elaeis* fruit.

*Elaeis* produces fruit within a fruit bunch. Each *Elaeis* tree produces approximately one fruit bunch per month for about 25 years. This ensures a constant and stable supply as compared with other annual crops. Each fruit bunch weighs from about 10 to 40 kilograms. The fruit bunch consists of fruit embedded in spikelets growing on a main stem. A single bunch contains multiple spikelets which cumulatively may contain as many as 3000 fruits. The individual fruit is reddish in color and about the size of a large plum, ranging in weight from 6 to 20 grams. The *Elaeis* fruit is made up of an outer skin (exocarp), a pulp (mesocarp) containing the palm oil in a fibrous matrix; a central nut consisting of a shell (endocarp); and the kernel, which itself contains oil having a different composition than the palm oil. The mesocarp comprises about 70-80% by weight of the fruit and about 45-50% of the mesocarp is oil. For every 100 kilograms of fruit bunches, typically 22 kilograms of palm oil and 1.6 kilograms of palm kernel oil can be extracted. The high oil yield from *Elaeis*, as high as 7,250 liters per hectare per year, makes it an effective source of oil.

The oil from *Elaeis* fruit is edible and has no known toxins. Palm oil is comprised of mainly triglycerides. Palmitic acid is the most abundant of the glycerides found in palm oil. Palmitic acid is a saturated fatty acid and hence palm oil is a viscous semi-solid, even at tropical ambient temperatures, and a solid fat in more temperate climates. Palm oil also contains minor components that are organically soluble, but not classified as oils. These include carotineoids, tocopherols, sterols, polar lipids and other fat-soluble impurities. The deep red color of palm oil is from the carotineoids in the palm oil.

Palm oil can be used in most food applications without hydrogenation. This reduces production cost by as much as 30% compared to other unsaturated oils. Palm oil is available in a variety of forms: crude palm oil, palm olein, palm stearin, refined bleached and deodorized palm oil, fractionated palm olein and palm mid-fraction. A range of products are available to suit a variety of manufacturing needs and in forms that are ready to use and require no further processing. These oil-based products are useful for cooking oil, food additives, feedstock additives, cosmetics, lubricants, fuel and soaps. In addition, the pulp and fibers from the processing of the fruit and bunches may be used as fodder (feedstock) for animals, fertilizer or as fuel.

*Elaeis* fruit must be processed in order to isolate and purify the oil within the mesocarp. The aim of processing palm oil is therefore to convert the crude oil to quality edible oil by reducing objectionable impurities to acceptable levels. Therefore, some compounds in the crude palm oil need to be removed or substantially reduced.

Palm oil mills are traditionally located near rivers from which water is taken for use in their processing operations. A number of palm oil mills conveniently discharge their POME into rivers, untreated. POME is a non-toxic, brownish, colloidal slurry of water, palm juice, oil and fine cellulosic fruit residue. POME contains appreciable amounts of N, P, K, Mg and Ca. POME also contains dissolved fatty acids, beta-carotenes and other nutritive components both fat soluble and water soluble. POME coming from the clarification process is usually at a temperature of between 80° C. and 90° C. and has a pH of from about 4 to about 5. POME has a very high biochemical oxygen demand and chemical oxygen demand, both of which are 100 times more than the oxygen demand from domestic sewage. This demand can create an environmental disaster in the waterways that the POME is discharged into.

The palm oil present in the effluent may float to the surface of the water body and form a wide-spread film which can prevent atmospheric oxygen from dissolving into its waters. Furthermore, when the organic load far exceeds its waste assimilation capacity, the available oxygen in the water body is rapidly consumed as a result of the natural biochemical processes that take place to break down the POME. The oxygen demand to break down the POME is so high that the water body may become completely devoid of dissolved oxygen. When this happens, anaerobic conditions are created in which hydrogen sulphide and other gases are generated and released into the environment resulting in objectionable odors. This riparian anaerobic condition will result in the decline and eventual destruction of aquatic life and the aquatic ecosystem.

If a convenient waterway is not available, POME is usually drained off into nearby evaporation pits and no further treatment of the POME is undertaken in most mills. The same anaerobic conditions form in these pits. The pits are eyesores and generate foul smelling gasses.

There are a few remediation techniques that are used to treat POME. One such remediation technique of POME involves anaerobic fermentation followed by aerobic fermentation in large ponds until the effluent quality is suitable for discharge. In some of the mills the treated effluent is used on the farm as manure and as a source of water for irrigation. The sludge accumulating in the fermentation ponds is periodically removed and fed to the land. In order to reduce the amount of POME, some mills employ expensive techniques such as de-watering and decanting centrifuges at various locations in the process line. These remediation techniques take a long time to finish and require additional human, industrial, economic and land resources. Therefore, the remediation techniques for POME are often not implemented at the palm oil mills.

POME is either disposed of at the expense of the environment or at the expense of the mills. Furthermore, valuable nutrients and oil are being discarded and put to no beneficial use. POME is a major environmental problem in Elaeis growing regions of the world. Valuable economic commodities are being thrown away.

Thus, there is a need in the palm oil processing industry to be able to reduce the amount of POME and to capture, and put to economic use, the nutrients and oil contained within POME and palm juice.

SUMMARY

Provided herein are methods for recovering and preserving POME by treating POME with antioxidants and harvesting useful compounds from the treated POME. Also provided herein are methods for treating the pressing products of *Elaeis* fruit with antioxidants and compositions derived from the treated pressing products.

In one aspect of the disclosure, a method for treating the effluent from the processing of *Elaeis* fruit comprises adding antioxidants to the effluent. In an embodiment, the antioxidants added to the effluent may be added in an amount sufficient to prevent spoilage therein. In an embodiment, the antioxidants added to the pressing products of *Elaeis* fruit may be added in an amount sufficient to prevent spoilage therein. In an embodiment, the antioxidants added to the POME and pressing products from *Elaeis* fruit may be added in an amount sufficient to prevent oxidation of POME and the pressing products from *Elaeis* fruit. A sufficient amount of antioxidants to be added will be apparent to one skilled in the art. In an embodiment of the present disclosure, the *Elaeis* comprises *Elaeis guineensis* and *Elaeis oleifera*. In another embodiment of the present disclosure, the antioxidants that are added to the pressing of *Elaeis* fruit are in an aqueous solution having a pH of from about 1.5 to about 4.0. In a preferred embodiment of the present disclosure, the antioxidants are derived from olive vegetation containing hydroxytyrosol in a concentration of from about 0.0005% to about 10% by weight. In a preferred embodiment of the present disclosure, the concentration of hydroxytyrosol is from about 0.5% to about 1.25% by weight. In yet another embodiment of the present disclosure, the antioxidants are added to POME within 12 hours from the processing of the *Elaeis* fruit.

In another aspect of the present disclosure, a method for increasing the antioxidant content of the pressing products of *Elaeis* fruit starts with pressing *Elaeis* fruit, then continues with adding an acidified aqueous antioxidants mixture having a pH of from about 1.5 to about 4.0 to the product of the pressing within 12 hours from the time of the pressing; then further continues by boiling the mixture of acidified aqueous antioxidants and pressing products and separating the aqueous layer and the organic layer of the boiled mixture of acidified aqueous antioxidants and pressing product. In an embodiment of the present disclosure, the antioxidants are added to *Elaeis* fruit before the pressing. In an embodiment of the present disclosure, the antioxidants are derived from olive vegetation having hydroxytyrosol in a concentration of from 0.0005% to 10% by weight and more preferably in a concentration of from 0.5% to 1.25% by weight. In another embodiment of the present disclosure, the separated organic layer and aqueous layers are dried by freeze drying. In yet another embodiment of the present disclosure, the dried layers may be used for an additive composition comprising a food additive, a feedstock additive, a dietary supplement additive, an antimicrobial additive, a soap additive, and a cosmetic additive. In an embodiment of the present disclosure, the dried layers may be used as a dietary supplement composition containing a weight ratio of hydroxytyrosol to oleoeuropein of between about 5:1 and about 200:1 or may additionally or separately contain a weight ratio of hydroxytyrosol and tyrosol of between about 3:1 and about 50:1. The dietary supplement may be a powder extract in the form of a tablet, capsule, pill or confection food additive.

In another aspect of the present disclosure a composition comprising the pressing products of *Elaeis* fruit and antioxidants is presented. In an embodiment of the present disclosure, the antioxidants are polyphenols derived from olives. In another embodiment of the present disclosure, the antioxidants are hydroxytyrosol derived from olives.

BRIEF DESCRIPTION OF THE DRAWING

FIG. 1: Structures of some antioxidant compounds found in olive oil.

DETAILED DESCRIPTION

All publications, patents, patent applications or other references cited in this application are herein incorporated by reference in their entirety as if each individual publication, patent, patent application or reference are specifically and individually indicated to be incorporated by reference.

Definitions

Unless otherwise indicated, all terms used herein have the same meaning as they would to one skilled in the art of the present invention. It is to be understood that this invention is not limited to the particular methodology, protocols, and reagents described, as these may vary.

"Oleuropein" is intended as secoiridoid glucoside oleuropein (Structure II in FIG. 1).

"Tyrosol" is intended as 4-hydroxyphenethyl alcohol (Structure VII in FIG. 1).

"Hydroxytyrosol" is intended as 3, 4-dihydroxyphenethyl alcohol (Structure VIII in the FIG. 1).

"Palm juice" is intended as any liquid and/or aqueous layer, any compounds, molecules and elements soluble therein that are derived from *Elaeis* fruit.

"Palm oil" is intended as any oil and/or organic layer and any compounds, molecules and elements soluble therein that are derived from *Elaeis* fruit.

"POME" is intended as palm oil mill effluent and refers to any effluent generated during the processing of palm oil.

"*Elaeis*" is intended as any species of Arecacae, any palm family, any oil palm, any hybrid plant species derived from or crossed with Arecacae.

"*Elaeis* fruit" is intended as any fruit from *Elaeis*.

"Pressing" is intended as any crushing, mashing, pulping or other means of disrupting the integrity of the *Elaeis* fruit.

POME Preservation

The processing of *Elaeis* fruit into edible palm oil consists of several steps. The first step is to harvest the fruit bunch. Harvesting involves cutting off the bunch from the tree and allowing it to fall to the ground by gravity. Fruits may be damaged in the process of pruning palm fronds to expose the bunch base to facilitate bunch cutting. As the bunch falls to the ground the impact further bruises the fruit. Bruising of the fruit increases the amount of free fatty acids. Free fatty acids are detrimental to the taste of the palm oil product and therefore care should be taken to avoid bruising during the harvesting of the fruit bunches. The fresh fruit contains enzymes capable of splitting the triglyceride contained in palm oil, into free fatty acid and other glycerides. When the bunch is cut, the enzymes start to catalyze and break down the oil into free fatty acids, mono and diglycerides. When the enzyme is in contact with the oil, the reaction is rapid. Thus, when the fruit is damaged, the oil released will be in contact with the enzyme and accordingly the free fatty acid content will increase. An additional problem encountered during the harvesting of the fruit is that it is often contaminated with dirt, sand and mud through its contact with the ground.

After harvesting, the fruit bunches are transported to a palm oil mill for processing. The next step in the processing of the fruit is to separate the fruit from the bunch structure. The fresh fruit bunch consists of fruit embedded in spikelets growing on a main stem. The separation of fruit from bunch happens in a mechanized threshing system consisting of a rotating drum equipped with bars that beat the bunches and detach the fruit from the bunch, leaving the spikelets on the stem.

Next, the free fruit and residual fruit bodies still within spikelets on the bunches are sterilized. The threshed fruits and bunches may be sterilized by being cooked in water or preferably through bathing them in a high-pressure steam. Whole bunches containing spikelets absorb a lot of water in the sterilization process. This absorption of water helps to separate any remaining fruit from the spikelets. After sterilization, the bunches are threshed again to further loosen any remaining fruits. The free fruits and the bunches are separated from each other. The empty bunches are then incinerated and the ash, a rich source of potassium, is returned to the plantation as fertilizer.

The sterilization process serves several purposes. First, from being in contact with the ground, the fruit bunches are contaminated with dirt and sand that contain a vast array of protozoans, bacteria, molds, fungi and other micro-organisms. The sterilization process kills all of these microorganisms to prevent spoilage due to infection. When the bunches are sterilized, the steam weakens the fruit stem and makes it easier to remove the fruit from the bunches upon shaking or tumbling in a threshing machine. Additionally, the heat helps to denature protein and pectin cross-linked matrices in which the oil-bearing cells are dispersed. The denaturing of the proteins causes the matrix in which the oil-bearing cells are dispersed to coagulate and thus the oil-bearing cells are free to combine into micro-pools that flow out of the pulp more easily during the pressing step. Sterilizing also weakens the pulp structure, making it easier to detach from the fibrous material in the fruit during the digestion process. The high heat partially disrupts the oil-containing cells in the mesocarp and permits oil to be released more readily in further processing steps. The moisture introduced by the steam acts to break down gums and resins. The gums and resins later cause undesirable foaming of the oil during frying. Some of the gums and resins are soluble in water. Others can be made soluble in water when broken down by hydrolytic reactions, and can then be removed during oil clarification. Starches present in the fruit are also removed in this way. The heat from the sterilization process causes the moisture in the nuts to expand. When the pressure is reduced the contraction of the nut leads to the detachment of the kernel from the shell wall, thus loosening the kernels within their shells. The detachment of the kernel from the shell wall greatly facilitates later nut cracking operations.

After sterilization, the fruit is digested. Digestion is the process of releasing the palm oil in the fruit through the rupture or breaking down of the oil-bearing cells. The digester consists of a steam-heated cylindrical vessel fitted with a central rotating shaft carrying a number of beater (stirring) arms. Through the action of the rotating beater arms, the fruit is pounded. Pounding the fruit helps to reduce the viscosity of the oil, destroys the exocarp, and furthers the disruption of the oil cells already begun in the sterilization phase.

After digesting, the fruit is pressed. There are two distinct methods of extracting oil from the digested material. One system uses mechanical presses and is called the dry method. The other is called the wet method and uses hot water to leach out the oil. In the dry method the objective of the extraction stage is to squeeze oil out of the digested fruit by applying mechanical pressure on the digested mash. There are a large number of different types of presses but the principle of operation is similar for each.

Specially designed screw-presses similar to those used for other oilseeds are most commonly used for the pressing of the digested fruit. These consist of a cylindrical perforated cage through which runs a closely fitting screw. Digested fruit is continuously conveyed through the cage towards an outlet restricted by a cone, which creates the pressure to expel the oil through the cage perforations.

The pressing products include an organic layer comprised of crude palm oil and other insoluble matter as well as an aqueous layer comprised of "palm juice" and other insoluble matter. The pressing product of *Elaeis* fruit contains multiple constituent products and compounds. Generally, the pressing products from *Elaeis* are distinguished as being either oil soluble or oil insoluble. For example, glycerides and other components of *Elaeis* fruit are either oil insoluble or oil soluble. Oil insoluble impurities from *Elaeis* fruit include fruit fibers, nut shells and free moisture. The majority of oil insoluble impurities are easily removed because they will separate into the aqueous layer when extracted with water. It is noteworthy that there is always some residual solubility of the organic (oil) layer in the aqueous (water) layer as well as the aqueous layer in the organic layer. Oil soluble non-glycerides in *Elaeis* fruit include free fatty acids, phospholipids, trace metals, carotenoids, tocopherols, tocotrienols, oxidation products and sterols. These impurities are generally detrimental to the flavor, odor, and color of the oil. They also contribute to the chemical reactions that cause the oil to become rancid. Multiple processing steps are required to remove these impurities.

A product of the pressing of *Elaeis* fruit is Palm juice. Palm juice as used herein is any aqueous liquid and any compounds, molecules and elements soluble therein that are derived from the *Elaeis* fruit. Palm juice includes both the inherent aqueous content of the *Elaeis* fruit as well as any aqueous content in the fruit as a result of a treatment or processing. Aqueous content may be introduced through steaming or cooking the fruit during the sterilization process, for example. Presently, methods are directed to processing only the organic layer. The aqueous layer is treated as a waste product.

The next step in the processing of the crude palm oil is to clarify the oil. The main point of clarification is to separate the oil from its ingrained impurities. The fluid coming out of the press is a mixture of palm oil, palm juice, water, cell debris, fibrous material and non-oily solids. Because of the non-oily solids, the mixture is highly viscous. Hot water is therefore added to the press output mixture to thin it so that it is easier to feed into the other processing steps. Water is usually added in a ratio of 3:1. The addition of water causes the heterogeneous solution to separate into an organic layer and an aqueous layer with an emulsion at the interface between the two layers. The emulsion consists of oil suspended in water with the aid of gums and resins. Facilitation of the separation of the layers into an organic layer and an aqueous layer and the destruction of the emulsion happens when heat is applied to the mixture. The heavy, non-oily solids fall to the bottom of the container in the aqueous layer while the lighter oil droplets flow through the aqueous layer into the top, organic layer.

The diluted mixture is passed through a screen to remove coarse fiber. The screened mixture is boiled from one to two hours and then allowed to settle by gravity in a tank so that the palm oil will separate and rise to the top. Because of the solubility coefficients of the oils and other compounds primarily within the organic layer, and the solubility coefficients of the palm juice and other compounds that are primarily within the aqueous layer, there are varying ratios of the products from the pressing in both the aqueous and the organic layer. For example, the aqueous layer is comprised of mainly water and palm juice, but also contains a significant amount of oils and other primarily oil soluble compounds, in amounts according to the solubility coefficient of each respective entity.

The clarified oil is then decanted into a reception tank. The aqueous layer is discarded as a waste product. The clarified oil still contains traces of water and dirt. To prevent increasing the concentration of free fatty acids through autocatalytic hydrolysis of the oil, the moisture content of the oil must be reduced down to approximately 0.15 to 0.25 percent by weight. Re-heating the decanted oil and skimming off the dried oil that rises to the surface, removes any engrained dirt and residual moisture.

In an alternative method of treating the purified oil from the clarification, any remaining foreign particles may be removed by centrifugation. The oil can then be vacuum dried to achieve a certain moisture content in the final product before being stored. The sludge produced from the oil clarification contains fibrous matter. This sludge is sent into a desander for the purpose of removing any sand which might adhere to the sludge so that the sand free sludge can be centrifuged to recover any oil loss in the sludge. The recovered oil is then clarified again. Then the remaining sludge is sent to an effluent treatment plant.

The purified and dried oil is then transferred to a tank for storage prior to being shipped away from the mill. Since the rate of oxidation of the oil increases with temperature and the oil is near 100° C. after clarification, the oil needs to be cooled as quickly as possible. However, it is preferred that the oil is maintained in a liquid state in order to prevent solidification and fractionation. Therefore, immediately after the clarification process, the oil is maintained at around 50° C. for storage. Iron contamination from the storage tank may occur if the tank is not lined with a suitable protective coating. Iron contamination is undesirable because it catalyzes reactions which break down the triglyceride structure of the fats forming free fatty acids and other products which introduce an off flavor into the palm oil. Citric acid is often added to the stored oil to chelate any iron cations. This chelation takes the iron out of solution and prevents the catalysis of undesirable reactions.

Although the water from the clarifying process still contains significant amounts of oil as well as most of the water soluble components from the *Elaeis* fruit, the water from the clarifier is considered waste. This waste is a major component of palm oil mill effluent (POME).

Large quantities of water are used during the crude oil extraction process. Up to about 1.5 cubic meters of water are used to process one ton of fruit bunches. From this quantity, about 50% of the water results in POME, the other 50% being lost as steam, mainly through sterilizer exhaust, piping leakages, as well as wash waters. Clarification of the extracted crude palm oil contributes about 60% of total POME.

Palm oil is generally preserved by destroying enzymes within the mesocarp during sterilization in order to prevent chemical changes to the oils therein, getting rid of as much water as possible from the isolated oil in order to prevent the growth of any micro-organisms and packaging the oil using sanitary best practices to prevent further contamination of the oil. These methods of preserving processed palm oil are not always practicable under the conditions of manufacture. Although the oil has been processed and purified, substantial autocatalytic events can still take place. These autocatalytic events are often a result of oxidation reactions and can cause the oil to spoil, becoming rancid over time. There is an existing need, therefore, to increase the resistance of palm oil to spoiling. It is also desirable to increase health benefits from the consumption of palm oil.

Resistance to spoilage, increasing nutritive value of the palm oil and harvesting the nutrients in palm juice and POME can be obtained through enrichment with antioxidants.

An antioxidant is a molecule capable of inhibiting the oxidation of other molecules. Oxidation is a chemical reaction that transfers electrons from a substance to an oxidizing agent. Oxidation reactions can produce free radicals. These free radicals have a very high reactivity and often will start chain reactions that damage whatever they are reacting with. Antioxidants terminate these chain reactions by removing free radical intermediates, and inhibit other oxidation reactions. They do this by being oxidized themselves, so antioxidants are often reducing agents (Sies 1997).

Natural antioxidants include polyphenols (for instance flavonoids and oleorupeins), ascorbic acid (vitamin C) and tocopherols (vitamin E), for example. Synthetic antioxidants include butylated hydroxyanisole, butylated hydroxytoluene, propyl gallate and ethoxyquin, among others.

One of the most powerful naturally occurring antioxidants is hydroxytyrosol, a type of polyphenol. Hydroxytyrosol may be obtained from olive oil juice during the production of olive oil according to the methods disclosed in U.S. Pat. Nos. 6,165,475, 6,197,308, 7,261,909 and 7,713,569 all to Crea, or Crea and Caglioti, all of which are expressly incorporated herein by reference.

In order for an antioxidant to be active, it must be soluble in the substance in which the free radicals or other oxidants exist. The effectiveness of water-soluble antioxidants is limited in preventing oxidation within fats as is the effectiveness of oil-soluble antioxidants limited in preventing oxidation within a water layer. However, antioxidants usually have some solubility in both the aqueous layer and the organic layer. The relative solubility of an antioxidant in an organic layer and an aqueous layer is referred to as a solubility coefficient. For example an antioxidant might have a solubility coefficient of 0.9 in water, this corresponds to 90% of the antioxidant being dissolved in the aqueous layer and 10% of the antioxidant being dissolved in the organic layer. Generally, the more polar an antioxidant molecule is, the more it will be soluble in the aqueous layer.

Palm oil, as commonly used, is low in beneficial antioxidants and other oils and compounds that are generally considered healthy. Olive oil, on the other hand, is known to consist of many different antioxidants and oils that are beneficial to the health of the consumer. Many people in Africa and Southeast Asia rely upon palm oil as their primary source of cooking oil. People throughout the world consume large amounts of palm oil as an additive to the processed foods that they consume. It would therefore be highly beneficial to the health of the inhabitants of Africa and Southeast Asia as well as consumers the world over, to increase the nutritive content of palm oil by adding the most health beneficial components of olive oil to the palm oil while at the same time preserving the wasted and/or oxidized healthy components within *Elaeis* fruit that are lost during processing.

Conventionally, olive oil production involves crushing olives, including the pits, to produce a thick paste. During this procedure, the crushed olives are continuously washed with water, a process known as malaxation. The paste is then mechanically pressed to squeeze out the oil content. In addition to providing olive oil, the pressing also squeezes out the paste's water content. Such washing and pressing steps yield a considerable amount of water, referred to as vegetation water.

Vegetation water can be used as a natural antibacterial, antiviral and/or fungicidal product for agricultural and/or pest control applications. It may also be used as a raw material for the production of oleuropein and other antioxidants useful for a variety of health purposes.

Both the pit and the pulp of olives are rich in water-soluble phenolic compounds. Such compounds are extracted from olives during malaxation and end up in the vegetation water according to their partition coefficients. Thus, various phenolic compounds, such as oleuropein and its derivatives, produced in olive pulp, can be found in abundance in vegetation water. Similarly, a number of monophenolic compounds, such as tyrosol and its derivatives, produced in olive pits, are also abundant in vegetation water.

Previously, Crea discovered that acidifying the vegetation water enhances storage stability, see U.S. Pat. No. 7,713,569 which is expressly incorporated herein by reference. Furthermore, the oleuropein contained in the vegetation water can be converted to hydroxytyrosol during this incubation. First, the pH of vegetation water is decreased to by the addition of acid. Without being limited as to theory, the addition of acid to the vegetation water appears to serve several purposes: (i) it stabilizes the vegetation water from air (oxygen) polymerization of phenolic molecules; (ii) it attenuates fermentation of the vegetation water by endogenous and/or exogenous bacteria and yeast; and (iii) it provides for the hydrolysis of oleuropein and other large phenolic molecules and conversion of such into hydroxytyrosol. Secondly, the acidified mixture is allowed to incubate until hydroxytyrosol is 75-90% of the total combination of oleuropein and hydroxytyrosol. Substantially all of the oleuropein in the original mixture is converted to hydroxytyrosol when the vegetation water is allowed to incubate under conditions which promote acid hydrolysis of oleuropein to hydroxytyrosol. The acidified vegetation water may be incubated for a period of at least two months, and even more preferably up to a period of approximately between 6-12 months. The sample may then be fractionated or extracted to separate hydroxytyrosol from other compounds. The separated hydroxytyrosol may then be dried for a future use such as treating the pressing product of *Elaeis* fruit.

Following the conversion of oleuropein to hydroxytyrosol, the incubated vegetation water may be purified or fractionated by any suitable method known in the art. Methods of fractionation include partitioning with an organic solvent, such as ethyl acetate, chromatographic methods, including gel chromatography and high pressure liquid chromatography (HPLC), or liquid extraction with supercritical fluids such as carbon dioxide. In other embodiments, the supercritical fluid is selected from methane, ethane, propane, butane, isobutane, ethene, propene, hydrofluorocarbons, tetrafluoromethane, chlorodifluoromethane, dinitrogen monoxide, sulphur hexafluoride, ammonia, and methyl chloride. It will be appreciated that more than one supercritical fluid may be used in combination.

As described above, the vegetation water is rich in water-soluble, phenolic compounds. Olive pulp extract contains about 6-9% total phenolic compounds by weight. The structures of the phenolic compounds and their precursors detected in olive oil are shown in FIG. 1: ligstroside (I); oleuropein glucoside (II); aglycone of ligstroside (III); aglycone of oleuropein glucoside (IV); dialdehydic form of ligstroside aglycone lacking a carboxymethyl group (V); dialdehydic form of oleuropein glucoside aglycone lacking a carboxymethyl group (VI); tyrosol (VII); and hydroxytyrosol (VIII). Hydroxytyrosol comprises about 40-50% of the total phenolic compounds in the olive pulp solid extract. It will be appreciated that an antioxidant mixture may include one, several, or all of the phenolic compositions in varying ratios.

In an embodiment, the present invention is for treating POME, palm oil and palm juice with antioxidants. Preferably the antioxidants are derived from olives. More preferably the antioxidants are rich in hydroxytyrosol derived from vegetation water from the processing of olive oil.

In a preferred embodiment, the method for treating POME from the processing of *Elaeis* fruit starts with adding antioxidants to the effluent from the processing of the palm oil. The *Elaeis* fruit is preferably from *Elaeis guineensis* or *Elaeis oleifera* but may be from any species of palm. The antioxidants may be any type of antioxidant, but are preferably derived from olive vegetation. The antioxidants from olive vegetation are in a liquid mixture with water that has been acidified such that the resulting aqueous mixture of antioxidants has a pH from about 1.5 to about 4.0. The antioxidants from the olive vegetation are a mixture of polyphenols that contain hydroxytyrosol having a concentration of from about 0.0005% to about 10% by weight of the mixture of polyphenols. A preferred range of the concentration of hydroxytyrosol is from about 0.005% to 5% by weight of the mixture of polyphenols. A more preferred range of the concentration of hydroxytyrosol is from about 0.05% to 2.5% by weight of the mixture of polyphenols. An even more preferred range of the concentration of hydroxytyrosol is from about 0.5% to 1.25% by weight of the mixture of polyphenols. The concentration of hydroxytyrosol in the added antioxidants may also be expressed as a ratio between hydroxytyrosol and another component. In an embodiment of the present invention, the ratio of hydroxytyrosol to oleoeuropein is between about 5:1 and about 200:1. In a preferred embodiment of the present invention, the ratio of hydroxytyrosol to oleoeuropein is between about 10:1 and about 100:1.

In an embodiment of the present invention, the acidified aqueous mixture of antioxidants are added to the effluent within about 12 hours from the time of the pressing of the *Elaeis* fruit. In another embodiment, the mixture of antioxidants are added to the *Elaeis* fruit before it is pressed. In a preferred embodiment, the mixture of antioxidants are added in-line with the pressing of the *Elaeis* fruit such that the pressing products are immediately mixed with the mixture of antioxidants.

In another embodiment of the present invention, the pressing product of *Elaeis* fruit is treated with acidified antioxidants from olive vegetation. The acidified antioxidants may be added only to the oil layer of the pressing product, only the aqueous layer of the pressing product, or to the entire pressing product. A preferred treatment of the pressing product of *Elaeis* fruit is to boil the pressing product with an acidified aqueous mixture of antioxidants derived from olive vegetation. The antioxidants from olive vegetation are in a liquid mixture with water or that has been acidified such that the resulting aqueous mixture of antioxidants has a pH from about 1.5 to about 4.0. The acid that is used to titrate the aqueous mixture of olive vegetation may be any acid. A preferred embodiment of the present invention uses any acid that is commonly used in the manufacture of food products, preferably citric acid.

In another embodiment of the present invention, the pressing products of *Elaeis* fruit are boiled with an acidified mixture of antioxidants that are added to the pressing products within 12 hours from the pressing of the *Elaeis* fruit. In a preferred embodiment, the acidified mixture of antioxidants are added to the pressing of the *Elaeis* fruit preceding the pressing of the *Elaeis* fruit or immediately thereafter. The boiling of the pressing product with the acidified mixture of antioxidants is useful for clarifying the oil layer. During the clarifying process, gums, resins and other emulsifying agents are removed from the oil and into the aqueous layer. After the pressing product has been boiled with the acidified aqueous mixture of antioxidants, the organic layer and the aqueous layer may be separated. The resulting organic layer and aqueous layers are enriched in antioxidants. The antioxidant enrichment helps to increase the resistance of the organic and aqueous layers to spoilage. The separated oil layer is then preferably dried through various means such as simmering the oil in a vat and then skimming off the film forming on the top surface or through vacuum drying. The aqueous layer is also dried by a variety of means. One preferred way of drying the aqueous layer is by freeze drying or lyophillizing. Whether dried or not, the oil and/or aqueous layer may then be used as a food additive, a feedstock additive, a cosmetic additive, a vitamin supplement, and an antimicrobial substance.

In another embodiment of the present invention, the antioxidant mixture of polyphenols may be added to the *Elaeis* fruit before the pressing. The antioxidant mixture is added to the fruit in either a liquid or solid form. During the pressing of the *Elaeis* fruit, the antioxidants mix into the pressing products. An advantage to this method of treating *Elaeis* fruit is that the pressing products do not have any opportunity to oxidize because the pressing products are immediately exposed to the antioxidant mixture. The pressing products are then preferably treated with an acidified aqueous layer of antioxidants. Preferably, the antioxidant enriched pressing products are then boiled with the acidified aqueous mixture of antioxidants to clarify the organic layer.

In yet another embodiment of the present invention, the added antioxidants and acid may be a heterogeneous mixture, a homogeneous mixture, a colloidal suspension or any other mixture of solids within solids or liquids in solids or liquids with liquids. The acid may be any acid but preferably enough citric acid is added to adjust the pH of the final mixture to a range of from about 1.5 to about 4.0. The products of the pressing of the *Elaeis* fruit and acidified antioxidant mixture may then be treated by boiling with water. In a preferred embodiment the products of the pressing of the *Elaeis* fruit and acidified antioxidant mixture are then treated by boiling with an acidified mixture of antioxidants having a pH of from about 1.5 to about 4.0. The acid may be an organic or inorganic acid other than citric acid or may be citric acid. Exemplary acids include the inorganic mineral acids; sulfuric, nitric, hydrochloric, and phosphoric acids; and organic acids such as carboxylic acids and phenols, for example.

In an embodiment of the present invention, a commercial source of antioxidants derived from vegetative waters of the pressing of olives may be used. One commercial source is Hidrox, available from Creagri Inc.

In an embodiment of the present invention, methods used to recover oils or other compounds of interest from POME, palm juice or palm oil include, but are not limited to, column chromatography, mixing with flocculants and/or zeolites, centrifuging, extracting, salting out or other means either chemical or physical.

In one exemplary embodiment, the isolated palm oil, palm juice or POME, or a concentrate or isolated fraction thereof, is administered to a mammalian subject, such as a person desirous of one or more of the benefits associated with oleuropeins, hydroxytyrosol or other antioxidants.

In another embodiment, the processed organic layer or aqueous layer obtained by the method of the invention can be administered orally or parenterally. Oral dosage forms can be in a solid or liquid form. Such dosage forms can be formulated from the processed organic and/or aqueous layer or they can be formulated from aqueous, organic or aqueous-alcoholic extracts. Regarding the latter, aqueous or aqueous-alcoholic (e.g., water-methanol or water-ethanol) extracts can be spray-dried to provide a dry powder that can be formulated into oral dosage forms with other pharmaceutically acceptable carriers.

In yet another embodiment, the solid oral dosage from compositions in accordance with this invention are prepared in a manner well known in the pharmaceutical arts, and comprise the processed organic layer and/or aqueous layer obtained by the method of the invention in combination with at least one pharmaceutically acceptable carrier. In making such compositions, the isolated product from the processing method of *Elaeis* fruit of the present invention, either in substantially pure form or as a component of a raw distillate or extract, are usually mixed, diluted or enclosed with a carrier. The carrier can be in a solid form, semi-solid or liquid material which acts as a vehicle, carrier or medium for the active ingredient. Alternatively, the carrier can be in the form of a capsule or other container to facilitate oral administration. Thus, the solid oral dosage forms for administration in accordance with the present invention can be in the form of tablets, pills, powders or soft or hard gelatin capsules.

Alternatively, the processed organic layer or aqueous layer obtained in accordance with this invention for oral administration can be in liquid form wherein the pharmaceutically acceptable carrier is water or an aqueous-alcoholic medium.

The compositions for administration in the present invention can also be formulated with other common pharmaceutically acceptable excipients, including lactose, dextrose, sucrose, sorbitol, mannitol, starches, gums, calcium silicate, microcrystalline cellulose, polyvinylpyrrolidone, methylcellulose, water, alcohol and the like. The formulations can additionally include lubricating agents such as talc, magnesium stearate and mineral oil, wetting agents, emulsifying and suspending agents, preserving agents such as methyl- and propylhydroxybenzoates, sweetening agents or flavoring agents. Further, the compositions of the present invention can be formulated so as to provide quick, sustained or delayed release of the active ingredient after administration to a subject.

Parenteral formulations for use in accordance with the present invention are prepared using standard techniques in the art. They are commonly prepared as sterile injectable solutions, using a parenterally acceptable carrier such as isotonic saline solution or as a sterile packaged powder prepared for reconstitution with sterile buffer or isotonic saline prior to administration to a subject.

In another embodiment, the preferred compositions of the present invention are comprised of a hydroxytyrosol-rich composition that is generated through the processing steps of (a) producing palm oil, palm juice and/or POME from *Elaeis* fruit; (b) adding oleuropein, hydroxytyrosol and other large phenolic molecules; (c) spray drying, i.e., evaporating the palm oil, palm juice and/or POME thereby resulting in a powder containing hydroxytyrosol. In another embodiment, the evaporation step described above is performed to preferably result in a powder containing approximately 1 to 5% hydroxytyrosol, and more preferably, a powder containing approximately 2% hydroxytyrosol.

In another aspect, the invention includes a dietary supplement comprising an aqueous extract of palm oil, palm juice or POME of the method of the present invention that contains a weight ratio of hydroxytyrosol to oleuropein of between 4:1 and 200:1, typically 10:1 and 100:1.

In a related aspect, the invention includes a dietary supplement comprising an aqueous extract of palm oil, palm juice or POME of the method of the present invention with a weight ratio of hydroxytyrosol and tyrosol of between 3:1 and 50:1, typically between 5:1 and 30:1.

The above supplements may be dried, preferably by spray drying, to provide a powder extract, which can be formulated into a tablet, capsule, pill, or confection food additive. Alternatively, the above supplements may be incorporated in pharmaceutical formulations such as into a hydroxytyrol-rich injectable formulation.

According to one related embodiment, the extract is an aqueous or aqueous-alcoholic extract. The extract may have a reduced moisture content to provide a concentrated liquid. Or, the extract may be dried to provide a powder. The extract may be in the form of a tablet, capsule, pill, or confection food additive.

Techniques suitable for concentrating and/or isolating oleuropein from aqueous and aqueous-alcoholic solutions are taught, for example, in U.S. Pat. Nos. 5,714,150, 6,416,808 and U.S. Application No. 2003/0108651 expressly incorporated herein by reference.

The invention provides, in one aspect, a hydroxytyrosol-rich composition from olive-derived vegetation water that is added to the product of the pressing of *Elaeis* fruit.

In yet another embodiment, the added antioxidants are comprised of substantially pure or pure hydroxytyrosol.

The present invention is not restricted to the processing of *Elaeis* fruit. It is equally applicable to the processing of fruit of an oil palm from a cross-breed and/or hybrid of *Elaeis*.

The present invention may also be practiced in connection with the processing of other vegetable edible oil fruits.

Example

Palm oil, palm juice and POME can be treated with antioxidants from olive juice by adding the antioxidants right after the pressing of the sterilized and digested fruit. The production of antioxidants containing hydroxytyrosol as used in the present invention can be accomplished as follows.

The pressing products of olives are put into a centrifuge. In a 1250 L plastic tote, waste water is collected directly from a centrifuge at a flow rate of about 60 gal/min. After 15 min., solid citric acid is poured into the collection tank and the solution is then stirred continuously. The addition of acid is completed in 15 min. After one hour from the addition of the acid, samples are collected and checked for pH. The pH is between 1.5 and 4.0. After incubation at room temperature for about 18 hours, the solution is then extracted with ethyl acetate. The organic layer is separated and column chromatography is performed upon the sample by adding it to a prepared column of silica. Fractions eluted from the column of silica are collected and analyzed for signature spectroscopic peaks corresponding to hydroxytyrosol as well as being analyzed using thin layer chromatography to detect for impurities. The fractions containing pure hydroxytyrosol are combined and concentrated by vacuum distillation.

This hydroxytyrosol is then added to a final concentration of 0.05% by weight to the product of a pressing of *Elaeis* fruit. The mixture of the pressing product of *Elaeis* fruit and the hydroxytyrosol are then processed further to separate the oil from the palm juice and/or POME according to well established methods of processing palm oil. Each isolated palm oil, palm juice and POME is enriched with hydroxytyrosol and thus the inherent nutritive components and oils are present because they are protected from oxidation and thus are more stable. After being isolated, the palm oil, palm juice and POME can then be dried down to an acceptable volume and used for a food supplement. The food supplement contains both the added hydroxytyrosol and compounds from *Elaeis*.

It is to be understood that the present invention has been described in detail by way of illustration and example in order to acquaint others skilled in the art with the invention, its principles, and its practical application. Further, the specific embodiments of the present invention as set forth are not intended as being exhaustive or limiting of the invention, and that many alternatives, modifications, and variations will be apparent to those skilled in the art in light of the foregoing examples and detailed description. Accordingly, this invention is intended to embrace all such alternatives, modifications, and variations that fall within the spirit and scope of the following claims. While some of the examples and descriptions above include some conclusions about the way the invention may function, the inventor does not intend to be bound by those conclusions and functions, but puts them forth only as possible explanations.

In light of the detailed description of the invention and the examples presented above, it can be appreciated that the several aspects of the invention are achieved.

The invention claimed is:

1. A method for producing one or more *Elaeis* fruit products with increased antioxidant content, comprising the steps of:
   (a) pressing an *Elaeis* fruit to form an *Elaeis* fruit pressing product,
   (b) adding an effective amount of antioxidants derived from olive vegetation to the pressed *Elaeis* fruit of step (a) within 12 hours from said pressing to form a mixture,
   (c) boiling the mixture of step (b),
   (d) separating the boiled mixture of step (c) into an aqueous layer comprising palm juice derived from the pressing of *Elaeis* fruit and an organic layer comprising palm oil derived from the pressing of *Elaeis* fruit, and
   (e) individually isolating the aqueous and organic layers to obtain one or more *Elaeis* fruit products with increased antioxidant content.

2. The method of claim 1, wherein the *Elaeis* fruit comprises one or more of *Elaeis guineensis* and *Elaeis oleifera*.

3. The method of claim 1, wherein said antioxidants are in a solid form.

4. The method of claim 1, wherein said antioxidants are in an aqueous solution having a pH of from about 1.5 to about 4.0.

5. The method of claim 1 wherein said antioxidants contain hydroxytyrosol in a concentration of from 0.0005% to 10% by weight.

6. The method of claim 1 wherein said antioxidants contain hydroxytyrosol at a concentration of from 0.5% to 1.25% by weight.

7. The method of claim 1, further comprising the step of freeze drying the isolated aqueous and organic layers.

8. A method for producing one or more *Elaeis* fruit products with increased antioxidant content, comprising the steps of:

(a) pressing an *Elaeis* fruit to form an *Elaeis* fruit pressing product, (b) adding an effective amount of antioxidants containing hydroxytyrosol to the pressed *Elaeis* fruit of step (a) within 12 hours from said pressing to form a mixture, (c) boiling the mixture of step (b), (d) separating the boiled mixture of step (c) into an aqueous layer comprising palm juice derived from the pressing of *Elaeis* fruit and an organic layer comprising palm oil derived from the pressing of *Elaeis* fruit, and (e) individually isolating the aqueous and organic layers to obtain one or more *Elaeis* fruit products with increased antioxidant content.

9. The method of claim 8 wherein said antioxidants contain hydroxytyrosol in a concentration of from 0.0005% to 10% by weight.

10. The method of claim 8 wherein said antioxidants contain hydroxytyrosol at a concentration of from 0.5% to 1.25% by weight.

* * * * *